United States Patent [19]

Bouchard et al.

[11] Patent Number: 5,376,138
[45] Date of Patent: Dec. 27, 1994

[54] HYDRAULIC DEVICE FOR CORRECTING THE GAIT OF A FEMORAL AMPUTEE

[75] Inventors: Jean-Claude Bouchard, Tavaux; Bernard Vera, Seurre, both of France

[73] Assignee: Etablissements Proteor SA, Dijon, France

[21] Appl. No.: 29,672

[22] Filed: Mar. 11, 1993

[30] Foreign Application Priority Data

Mar. 11, 1992 [FR] France ............... 92 02901

[51] Int. Cl.$^5$ ............... A61F 2/64; A61F 2/74
[52] U.S. Cl. ............... 623/44; 623/43; 188/315; 188/322.19; 188/322.13
[58] Field of Search ............... 623/26, 43, 44, 45, 623/39, 46; 188/315, 322.15, 322.19, 280, 322.13, 322.14

[56] References Cited

U.S. PATENT DOCUMENTS 2,561,370 7/1951 Henschke et al. ............... 623/44 X
3,316,558 5/1967 Mortensen.
4,973,077 11/1990 Kuwayama et al. ............... 280/689

FOREIGN PATENT DOCUMENTS 0097226 1/1984 European Pat. Off..
1077650 11/1954 France ............... 188/316
1565589 3/1968 France.
724959 7/1942 Germany.
1075277 8/1960 Germany.
0598608 3/1978 U.S.S.R. ............... 623/26

Primary Examiner—David H. Willse
Attorney, Agent, or Firm—Scully, Scott, Murphy & Presser

[57] ABSTRACT

A device has a valve (21) activated by hydraulic fluid in opposition to a resilient restoring element (27) and blocking off an outlet in the bottom of a cylinder (3) when the fluid, responsive to being compressed by a piston (5), exerts a specified pressure subsequent to an involuntary movement on the part of a femoral amputee wearing the device so as to correct the gait of the amputee.

7 Claims, 5 Drawing Sheets

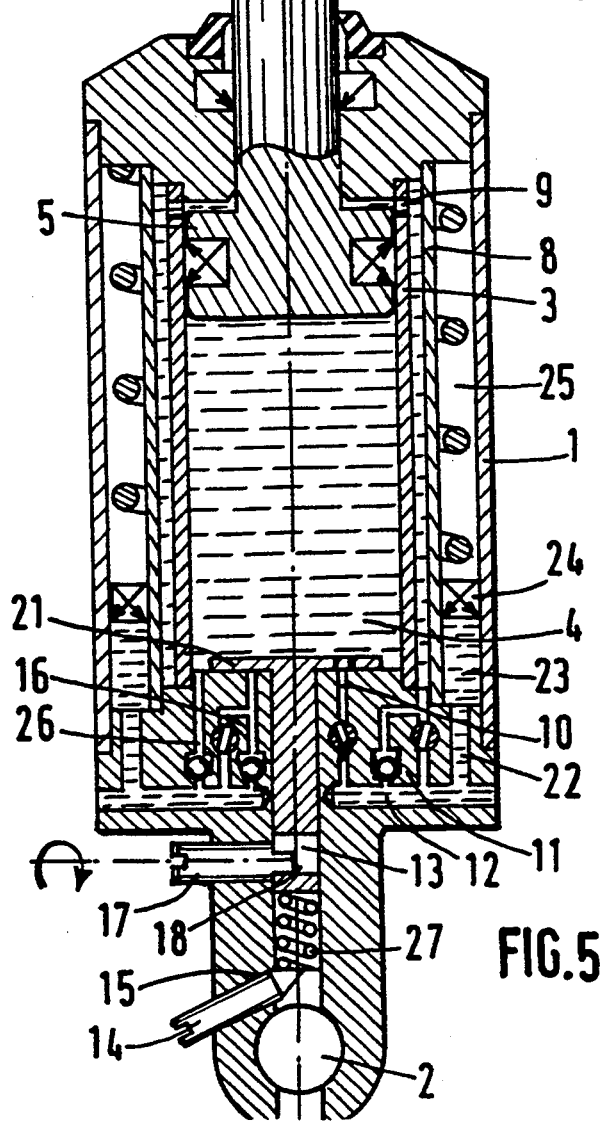
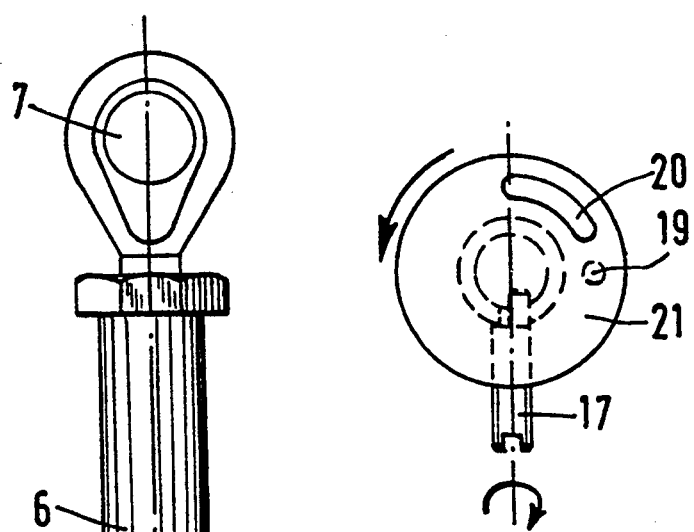
FIG. 8
FIG. 5

HYDRAULIC DEVICE FOR CORRECTING THE GAIT OF A FEMORAL AMPUTEE

BACKGROUND OF THE INVENTION

1. Field of the Invention

The present invention relates to a hydraulic device for correcting the gait or walk of a femoral amputee.

2. Discussion of the Prior Art

As is known in the technology, the stump of the thigh of an amputee who is equipped with a prosthetic leg fits into a matching depression, generally referred to as a socket, which in turn, is articulated to the leg of the amputee. There is usually provided a hydraulic shock absorber which regulates or controls the gait or movement of the amputee between the socket and the leg of the amputee. The shock absorber includes a piston rod and a cylinder, whereby the piston rod is attached to the socket and the cylinder attached to the leg, or vice versa. Hydraulic fluid which is provided within the shock absorber assists the wearer thereof to extent and flex the leg. The shock absorber is particularly resistant to flexion during every phase or situation of walking movement, and especially in the event of a misstep by the amputee.

SUMMARY OF THE INVENTION

Accordingly, it is an object of the present invention to provide an improvement with regard to such a hydraulic walking motion or gait-correcting device in that there is applied a constant and controlled braking force in the event of the fall of the wearer.

Another object of the present invention resides in improving upon such a hydraulic gait-correcting device in which the pressure of the hydraulic fluid which generates the braking force can be correlated with the physical capacities or conditions of the wearer.

The foregoing and other objects are attained, pursuant to the invention, in a hydraulic device for regulating or correcting the gait or walking movement of a femoral amputee; wherein the device is in the form of a shock absorber with, firstly, a piston which moves into and out of a cylinder and resultingly compresses and decompresses a hydraulic fluid; secondly, a fluid-circulating system which, through at least one opening, opens onto a flat area located at one end of the cylinder and communicates with the other end of the cylinder, and thirdly, a reservoir which communicates with the circulatory or fluid flow system and accommodates fluid compressed by another piston subject to resilient restoring or biasing means, and whereby either the first-mentioned piston is attached to a socket accommodating the stump of an amputated leg and a housing of the device is attached to a prosthetic leg articulated to the socket, or conversely. A valve is activated by the hydraulic fluid in opposition to the force of further resilient restoring means, such as a spring, and blocks off the opening when the wearer moves involuntarily, and in which the fluid upon being compressed by the first piston, exerts a specified pressure, and further includes another fluid-circulating system operating partly independently of the first system and which incorporates a variable escape branch conduit or bypass which is openable below the valve.

The valve itself can be provided with a slot, and means are provided for either aligning or bringing out of alignment the slot with respectively the associated or second opening of the variable escape branch.

The resilient means for restoring the valve are preferably operable so as to be variable, enabling the device to be adapted to the degree of physical independence of the amputee.

A variable operating system for maintaining the value in the state in which it blocks off the first opening will also be preferably provided so that the amputee can, at will, either retard or facilitate an increase in the circulation of fluid through the second opening. Any braking motion encountered will be opposed by the motion of the piston as long as the second opening remains free. This feature, for example, is of advantage to the amputee descending a stairway. The piston is maintained in the compressive phase thereof as long as both openings are blocked off.

BRIEF DESCRIPTION OF THE DRAWINGS

Reference may now be had to an exemplary embodiment of the invention taken in conjunction with the accompanying drawings; in which:

FIG. 5 illustrates a longitudinal sectional view through the device in which the latter has been intentionally entirely deactivated;

FIG. 6 illustrates a plan view of part of the upper surface of the valve of the device during the operating phases represented by respectively FIGS. 1, 2 and 3;

FIG. 8 illustrates a view similar to that of FIG. 6 during the operating phase represented by FIG. 5.

DETAILED DESCRIPTION

Figure 1:
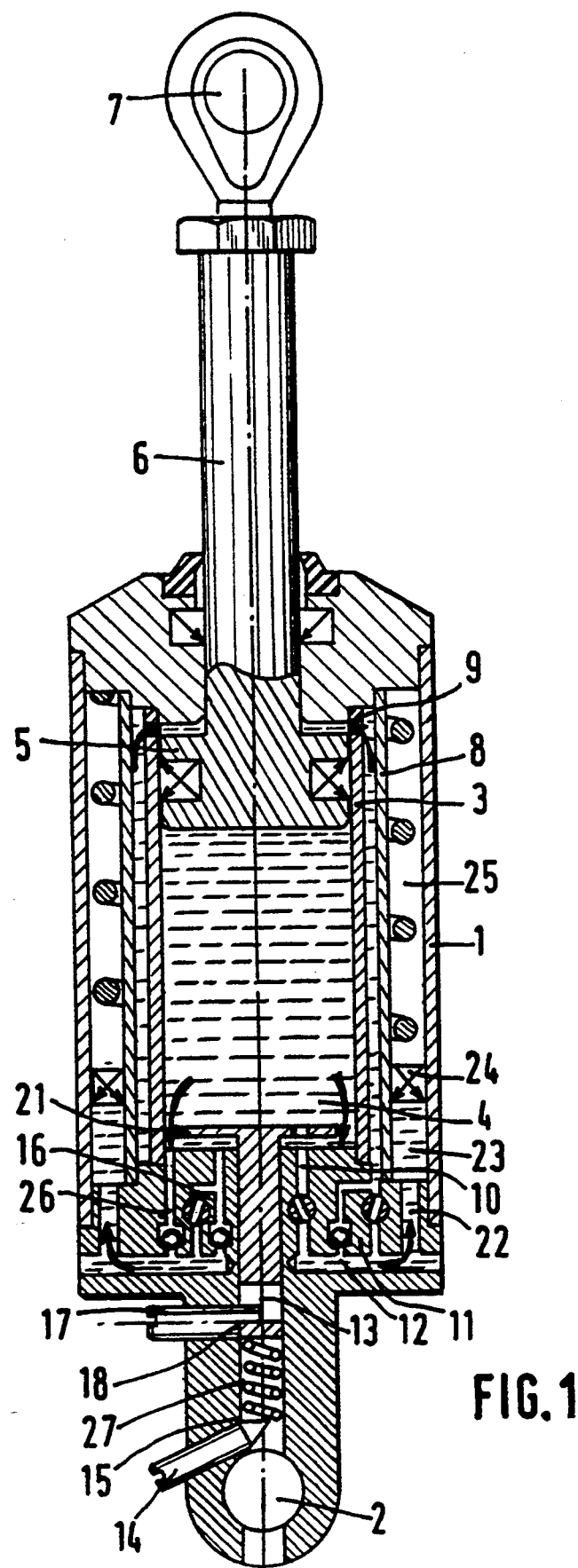
FIG. 1 illustrates a longitudinal sectional view through a device constructed in accordance with the present invention, in a mode wherein an amputee is walking normally and a piston of the device is compressing the hydraulic fluid therein.
Figure 2:
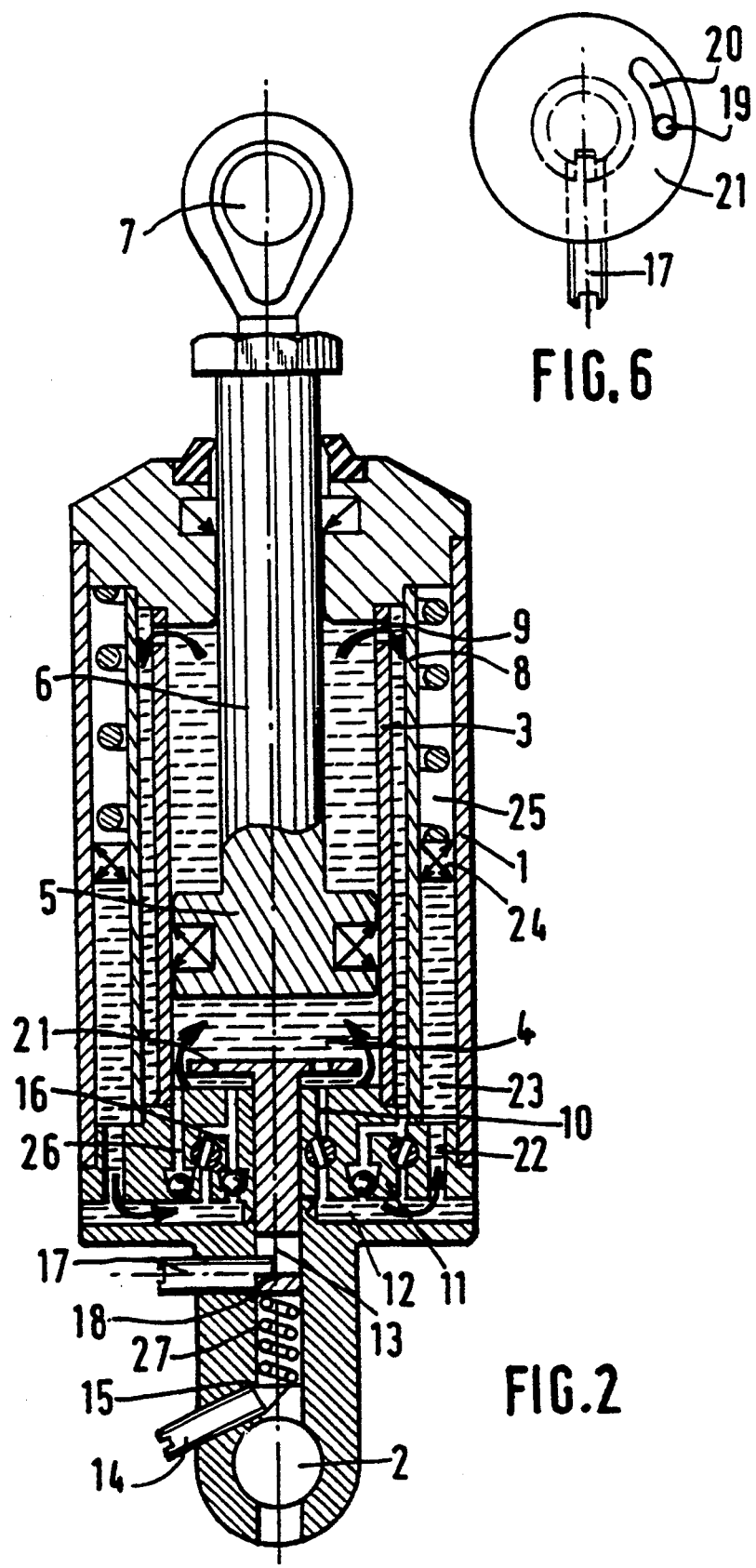
FIG. 2 illustrates a longitudinal sectional view while the amputee is walking normally and with the piston decompressing the fluid.
Figure 3:
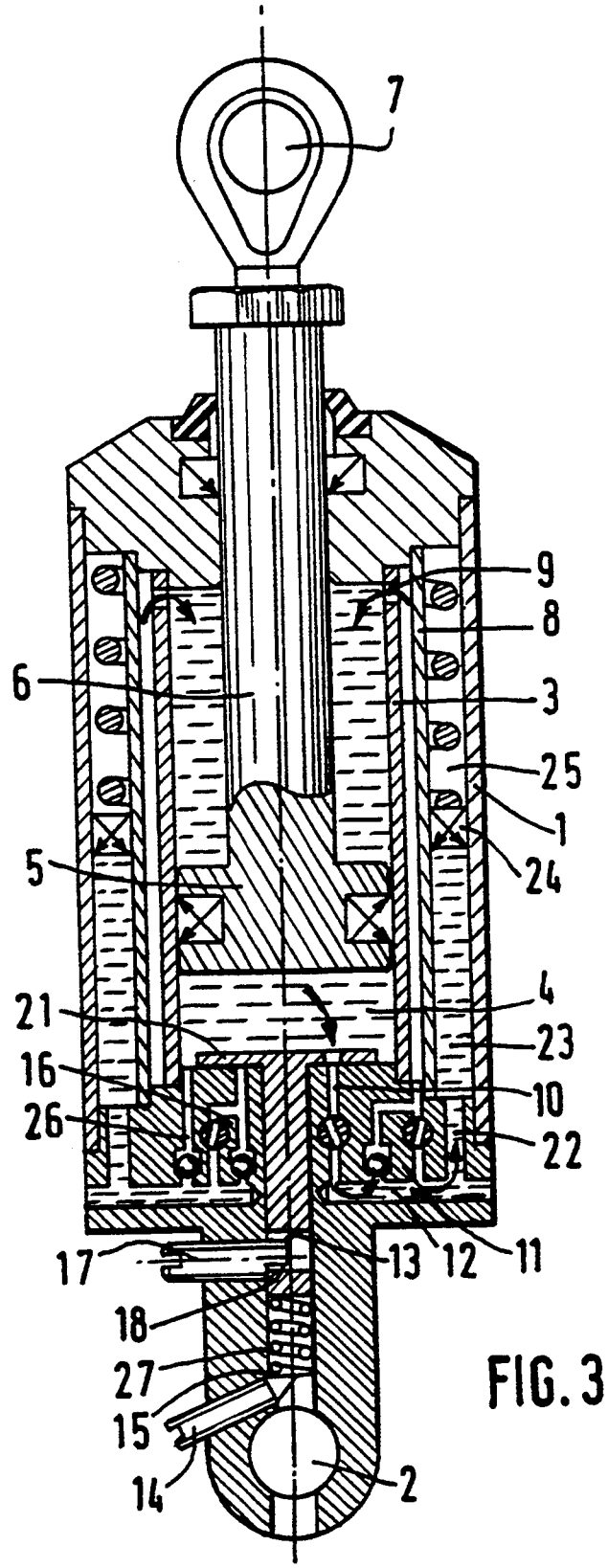
FIG. 3 illustrates a longitudinal sectional view representing the device in operation, and in which the amputee has lost his balance subsequent to an involuntary movement.
Figure 7:
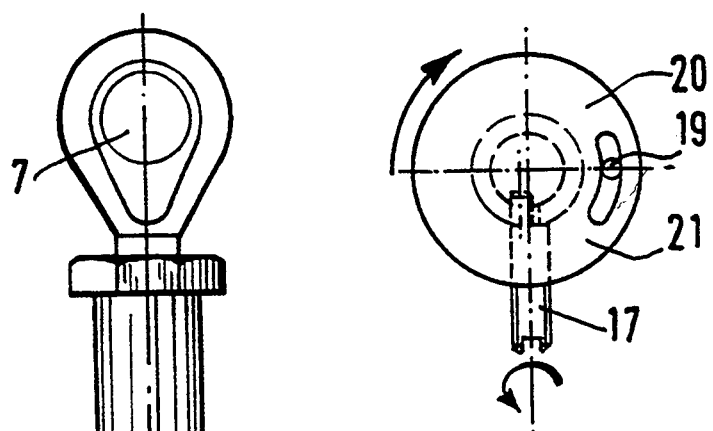
FIG. 7 illustrates a view similar to that of FIG. 6 during the operating phase represented by FIG. 4.

The hydraulic device illustrated in FIGS. 1 and 2 of the drawings is in the form of a shock absorber. One end of a housing 1 is attached by means of a pivot joint 2 to a prosthetic leg (not shown) worn by a femoral amputee. Centrally accommodated within the housing 1 is a first cylinder 3 containing hydraulic fluid 4. A piston 5 is adapted to travel reciprocatingly into and out of the cylinder 3. A piston rod 6 extends from piston 5 and out of first cylinder 3 and is attached by means of a pivot joint 7 to a socket (not shown) which accommodates the stump of the leg of the amputee. Alternatively, the housing 1 can just as well be attached to the socket and the piston rod 6 to the leg. The socket and leg are conventionally articulated to each other, as is known in this technology.

Cylinder 3 is concentrically accommodated within an outer cylinder 8. The two cylinders 3, 8 communicate with each other at the top or upper ends through openings 9 formed in the wall of inner cylinder 3 and at the bottom end through a channel 12 with branch conduits 10, 16 and 26 which open into the bottom of inner cylinder 3 and a branch conduit 11 which opens into the bottom of outer cylinder 8.

A valve 21 is mounted on a valve rod 13 which is activated by hydraulic fluid 4 in opposition to the force of resilient restoring means 27, such as a spring. The resilient restoring 27 engage the end of valve sod 13 opposite the end mounting the valve 21. Valve 21 is adapted to block off the outlets of branch conduits 10 and 16 leading into the bottom of the first or inner cylinder 3. A screw 14, which is actuatable from the exterior of the device, displaces a disk 15 against which there contacts resilient restoring means 27, thereby varying the tension and compression the means 27 exert against valve 21.

Valve 21 can be rotated through the intermediary of a rotatable catch or eccentric wheel 17 which engages a depression 18 formed in valve rod 13 and extends laterally outwardly of the device. Branch conduit 10 constitutes a variable escape or bypass branch conduit which communicates with channel 12 and opens into the bottom of inner cylinder 3 through an outlet 19, as shown in FIG. 6. Extending perpendicular to outlet 19 is a slot 20 in the shape of an arc of a circle formed in valve 21. Channel 12 is adapted to communicate with inner cylinder 3 by means of conduit 10 depending upon the particular position of valve 21 even under conditions in which the valve is supported against the bottom of the cylinder 3.

Channel 12 also communicates with a reservoir 23 of an annular cross-section located between cylinders 3 and 8. Resting against the fluid in reservoir 23, and subjected to the biasing force of resilient restoring means 25, which is in the form of a spring, is an annular piston 24. The other end of resilient restoring means 25 is supported against the inner surface of the top of housing 1.

The manner in which the device operates is now described as follows:

As long as the amputee is walking normally with the stump of his amputated leg accommodated in a socket being articulated to a prosthetic leg through a device constructed in accordance with the invention, for adjusting his gait or walking motion, valve 21 will be displaced from the bottom of inner cylinder 3, as illustrated in FIGS. 1 and 2. The hydraulic fluid, consequently, will be circulating conventionally, as indicated by the arrows, as subjected to the force acting on piston 5 between cylinders 3 and 8 on each side of piston 5 and between the cylinders and reservoir 23 whether the fluid is being compressed (FIG. 1) or decompressed (FIG. 2) by the piston. A quantity of the fluid will fill the space of variable escape or discharge branch conduit 10.

If the wearer missteps and; for example, falls down, piston 5 is then rapidly moved and the rapidly displaced and highly compressed fluid will force valve 21 against the base of inner cylinder 3, thereby shutting off the outlets of branch conduits 16. The outlet 19 in variable branch conduit 10, however, will be in operative alignment with the slot 20 in valve 21, and the fluid can remain in variable escape branch conduit 10, thereby braking the descent of piston 5. The level of pressure necessary to force valve 21 into contact against the bottom of inner cylinder 3 can be previously specified, and easily adapted to the amputee's level of independence by means of the adjusting screw 14.

Figure 4:
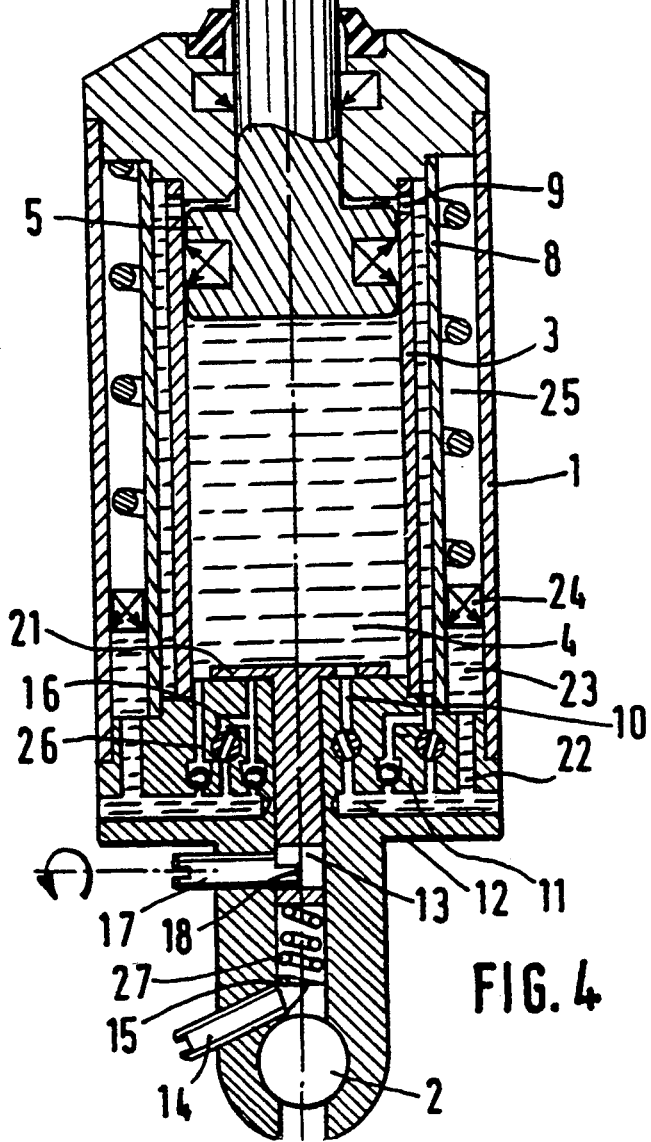
FIG. 4 illustrates a longitudinal sectional view through the device, in which the latter has been intentionally partly deactivated to facilitate the amputee descending a stairway.

If the amputee needs to partly deactivate the device in order to be able to carry out certain movements; for instance, such as descending a stairway, he can block off the access of fluid to all channels or conduits, with the exception of variable escape branch conduit 10 (FIG. 4), by rotating the eccentric wheel 17 either clockwise or counterclockwise to simultaneously lower and rotate valve 21 while permitting the variable escape or bypass branch conduit 10 to remain in communication with slot 20 through outlet 19.

Finally, if the amputee needs to or at least wishes to completely deactivate the device (FIG. 5), he can rotate eccentric wheel 17 in an opposite direction so as to lower valve 21 until the latter blocks off the outlet 19 of slot 20 (FIG. 6), with the extension thereof always being available by means of resilient restoring means or spring 25.

In summation, the invention accordingly provides simply implementable but significant improvements in a hydraulic device for regulating or correcting the gait of a femoral amputee.

We claim:

1. A hydraulic device for regulating or correcting the gait of a femoral amputee, comprising a shock absorber including a first cylinder (3); a first piston traveling into and out of said cylinder (3) for compressing and decompressing a hydraulic fluid, a fluid-circulating system (8, 9, 11 and 16) opening through at least one outlet onto a flat area formed at one end of said cylinder (3) and operatively communicating with the other end of said cylinder, a reservoir (23) communicating with the fluid-circulating system for accommodating hydraulic fluid, a second piston including first resilient restoring means for exerting a biasing force thereagainst so as to compress said hydraulic fluid, said first piston being attached to a socket accommodating a stump of an amputated leg and a housing (1) of the device being attached to a prosthetic leg articulated to the socket or conversely, second resilient restoring means (27), a valve (21) activated by the hydraulic fluid in opposition to the force of said second resilient restoring means (27) for blocking off said outlet when the wearer moves involuntarily and the hydraulic fluid upon compression by the first piston (5) exerting a specified pressure, and a second fluid-circulating system operating partly independently of the first fluid-circulating system comprising a variable escape branch circuit (10) having an outlet below the valve (21) and enabling selective discharge of hydraulic fluid therethrough during various modes in the gait of the amputee.

2. A device as claimed in claim 1, wherein said hydraulic fluid circulates from one side of the first piston (5) to the other through a second cylinder (8) which has the first cylinder (3) concentrically arranged therein.

3. A device as claimed in claim 1 or 2, wherein reservoir (23) has an annular cross-section and is concentrically arranged with the first cylinder (3).

4. A device as claimed in claim 3, wherein said valve (21) has a slot (20) formed therein, and actuating means (17) for displacing the valve for aligning the slot with the outlet (19) of the variable escape branch conduit (10) below the valve.

5. A device as claimed in claim 4, wherein said activating means for the valve (21) displaces said valve against outlets of said first and second hydraulic-fluid circulating systems.

6. A device as claimed in claim 1, compressing means for varying the tension of the resilient restoring means (27) for the valve (21).

7. A device as claimed in claim 1, wherein said first and second resilient restoring means each comprises a compression spring.

* * * * *

UNITED STATES PATENT AND TRADEMARK OFFICE
CERTIFICATE OF CORRECTION

PATENT NO. :   5,376,138
DATED      :   December 27, 1994
INVENTOR(S):   Jean-Claude Bouchard, et al.

It is certified that error appears in the above-indentified patent and that said Letters Patent is hereby corrected as shown below:

Column 3, line 9:   "sod"   should read --rod--

Column 4, line 62, Claim 6:   "compressing"

should read --comprising--

Signed and Sealed this

Twelfth Day of September, 1995

Attest:

BRUCE LEHMAN

Attesting Officer      Commissioner of Patents and Trademarks